US008133864B2

(12) United States Patent
Ishiwata et al.

(10) Patent No.: US 8,133,864 B2
(45) Date of Patent: Mar. 13, 2012

(54) PAR-2 AGONIST

(75) Inventors: Hiroyuki Ishiwata, Chiba (JP);
Mototsugu Kabeya, Tokyo (JP); Toru Kanke, Tokyo (JP)

(73) Assignee: Kowa Company, Ltd., Nagoya-shi (JP)

( * ) Notice: Subject to any disclaimer, the term of this patent is extended or adjusted under 35 U.S.C. 154(b) by 641 days.

(21) Appl. No.: 11/909,931

(22) PCT Filed: Mar. 29, 2006

(86) PCT No.: PCT/JP2006/306433
§ 371 (c)(1),
(2), (4) Date: Mar. 17, 2009

(87) PCT Pub. No.: WO2006/104190
PCT Pub. Date: Oct. 5, 2006

(65) Prior Publication Data
US 2009/0215703 A1    Aug. 27, 2009

Related U.S. Application Data

(60) Provisional application No. 60/665,831, filed on Mar. 29, 2005.

(51) Int. Cl.
*A61K 38/08* (2006.01)
*C07K 5/083* (2006.01)
*C07K 5/087* (2006.01)

(52) U.S. Cl. ............... 514/13.2; 514/15.4; 514/15.6; 514/16.4; 514/16.7; 514/20.6; 514/20.8; 514/21.9; 530/330

(58) Field of Classification Search .............. None
See application file for complete search history.

(56) References Cited

U.S. PATENT DOCUMENTS

| 5,763,575 A | 6/1998 | Sundelin et al. |
| 5,874,400 A | 2/1999 | Sundelin et al. |
| 5,888,529 A | 3/1999 | Bunnett et al. |
| 5,958,407 A | 9/1999 | Bunnett et al. |

FOREIGN PATENT DOCUMENTS

| JP | 2001-064203 A | 3/2001 |
| JP | 2001-181208 A | 7/2001 |
| JP | 2001-233790 A | 8/2001 |
| WO | WO 96/23225 A1 | 8/1996 |
| WO | WO 01/47556 A1 | 7/2001 |
| WO | WO 01/62291 A1 | 8/2001 |
| WO | WO 03/104268 A1 | 12/2003 |
| WO | WO 2006/070780 A1 | 7/2006 |

OTHER PUBLICATIONS

International Preliminary Report on Patentability dated Nov. 22, 2007, issued in corresponding PCT/JP2006/306433, with Form PCT/IB/338.
Vincenzo Santagada et al., "Minimal Structural Requirements for Agonist Activity of PAR-2 Activating Peptides", Bioorganic & Medical Chemistry Letters 12, pp. 21-24, 2002.

Sverker Nystedt et al., "Molecular Cloning of a Potential Proteinase Activated Receptor", Proceedings of the National Academy of Sciences USA 91, pp. 9208-9212, 1994.
Scott R. Macfarlane et al., "Proteinase-Activated Receptors", Pharmacological Reviews, vol. 53, No. 2, pp. 245-282, 2001.
Samir S. Roy et al., "Dual endothelium-dependent vascular activities of proteinase activated receptor-2-activating peptides: evidence for receptor heterogeneity", British Journal of Pharmacology 123, pp. 1434-1440, 1998.
Atsufumi Kawabata et al., "Increased vascular permeability by a specific agonist of protease-activated receptor-2 in rat hindpaw", British Journal of Pharmacology 125, pp. 419-422, 1998.
Bahjat Al-Ani et al., Proteinase-Activated Receptor 2 ($PAR_2$): Development of a Ligand-Binding Assay Correlating with Activation of $PAR_2$ by $PAR_1$—and $PAR_2$-Derived Peptide Ligands, The Journal of Phamacology, The Journal of Pharmacology and Experimental Therapeutics 290, pp. 753-760, 1999.
Morley D. Hollenberg et al., "Proteinase-Activated Receptor-2 in Rat Aorta: Structural Requirements for Agonist Activity of Receptor-Activating Peptides", Molecular Pharmacology, 49, pp. 229-233, 1996.
John J. MeGuirre et aL, "2-Furoyl-LIGRLO-amide: A Potent and Selective Proteinase—Activated Receptor 2 Agonist", The Journal of Pharmacology and Experimental Therapeutics, vol. 309, No. 3, Jun. 2004, pp. 1124-1131.

(Continued)

*Primary Examiner* — Jeffrey E Russel
(74) *Attorney, Agent, or Firm* — Westerman, Hattori, Daniels & Adrian LLP

(57) ABSTRACT

The present invention relates to a pharmaceutical composition for preventing/treating conditions associated with PAR-2. The present invention also relates to a method for preventing/treating the condition using the pharmaceutical composition and use for manufacturing the pharmaceutical composition. The pharmaceutical composition comprises a compound represented by the following general formula (1), salt or solvate thereof and a pharmaceutically acceptable carrier: Ar—CO—$AA_1$—$AA_2$—$AA_3$—$AA_4$—NH—X—Y (1) wherein, Ar represents a phenyl group or an aromatic heterocyclic group optionally having substituent(s): $AA_1$ represents a hydrophobic amino acid: $AA_2$ represents an amino acid absent of substituent(s) having more than two carbon atoms: $AA_3$ represents an amino acid absent of substituent(s) having more than two carbon atoms: $AA_4$ represents a basic amino acid: X represents a straight chain or branched bivalent saturated aliphatic hydrocarbon group having 1 to 6 carbon atoms: Y represents basic substituent(s); straight chain, branched, or cyclic bivalent saturated aliphatic hydrocarbon group having 1 to 6 carbon atoms; or an aromatic hydrocarbon group having 6 to 10 carbon atoms. The compound represented by the general formula (1) has dramatically improved PAR-2 activation potency compared to peptide comprised of 6 amino acids (Tethered receptor agonist peptide: TRAP) in spite of reduction of the number of amino acid.

16 Claims, No Drawings

OTHER PUBLICATIONS

Hashem N. Aishurafa et al., "A protease activated receptor-2 (PAR-2) activating peptide, tc-LIGRLO-NH$_2$, induces protease release from mast-cells: role in TNF degradation", BMC Pharmacology, vol. 4, No. 12, Jul. 2004, pp. 1-9.

Toni Kanke et at, "Characterization of Potent Protease-Activated Receptor-2 (PAR-2) Activating Peptide, 2-ftroyl-LIGRL-NH$_2$," Kowa Tokyo New Drug Research Laboratories II, Div.; p. 116.

(Graeme S. Cottrell ct al., "Trypsin N, a Novel Agonist of Protease-activated Receptors 2 and 4", The Journal of Biological Chemistry, vol. 279, No. 14, Apr. 2004, pp. 13532-13539.

European Search Report dated Jun. 17, 2009 issued in corresponding European Application No. 06730381.8.

Hollenberg M. D. et al., "Proteinase-Activated Receptors: Structural Requirements for Activity, Receptor Cross-Reactivity, and Receptor Selectivity of Receptor-Activating Peptides", Canadian Journal of Physiology and Pharmacology, 1997, pp. 832-841, vol. 75.

European Search Report dated Jul. 6, 2009 issued in corresponding European Application No. 5822433.8.

Hollenberg, M. D. et al., "Proteinase-Activated Receptors: Structural Requirements for Activity, Receptor Cross-Reactivity, and Receptor Selectivity of Receptor-Activating Peptides", Canadian Journal of Physiology and Pharmacology, Jul. 1997, pp. 832-841, vol. 75.

Lashuel, H. A. et al., "Protofilaments, Filaments, Ribbons, and Fibrils from Peptidomimetic Self-Assembly: Implications for Amyloid Fibril Formation and Materials Science", Journal of the American Chemical Society, May 19, 2000, pp. 5262-5277, vol. 122, American Chemical Society.

S. Vincenzo et al.; "Minimal structural requirements for agonist activity of PAR-2 activating peptides, Bioorganie & Medicinal Chemistry Letters", vol. 12, No. 1, pp. 21-24, 2001.

International Search Report of PCT/JP2006/306433, date of mailing Apr. 25, 2006.

SEQUENCE LISTING

<160> NUMBER OF SEQ ID NOS: 2

<210> SEQ ID NO 1
<211> LENGTH: 6
<212> TYPE: PRT

```
<213> ORGANISM: Artificial Sequence
<220> FEATURE:
<223> OTHER INFORMATION: Chemically Synthesized Peptide

<400> SEQUENCE: 1

Ser Leu Ile Gly Lys Val
1               5

<210> SEQ ID NO 2
<211> LENGTH: 6
<212> TYPE: PRT
<213> ORGANISM: Artificial Sequence
<220> FEATURE:
<223> OTHER INFORMATION: Chemically Synthesized Peptide

<400> SEQUENCE: 2

Ser Leu Ile Gly Arg Leu
1               5
```

PAR-2 AGONIST

DESCRIPTION

PAR-2 Agonist

TECHNICAL FIELD

The present invention relates to PAR-2 agonist, and a pharmaceutical composition containing the PAR-2 agonist as an active ingredient for preventing/treating PAR-2 associated diseases, particularly the present invention relates to PAR-2 agonist useful for development of a pharmaceutical preparation as well as prevention of development or progress, amelioration, and treatment of conditions such as fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

PAR (Protease-activated receptor)-2 is one of the protease-activated receptor (PAR) belonging to the G protein-coupled receptor family of 7 transmembrane type cloned in 1994 by Nystedt et al. (Proc. Natl. Acad. Sci. USA, 1994, 91, 9208-9212). PAR is a receptor family characterized by its activation occurred when a specific site of amino-acid sequence of the N-terminus of the molecule is cleaved by serine protease such as thrombin or trypsin and a new N-terminal fragment bind to ligand binding site of the molecule itself. To date, four types of PARs: PAR-1, PAR-2, PAR-3 and PAR-4, have been cloned; and each of PAR-1, PAR-3 and PAR-4 has been revealed its function as receptor related to platelet aggregation induced by thrombin. PAR-2 shares a number of similarities in structure and activation mechanism with other PARs; however, functional differences between PAR-2 and other PARs are suggested, for example, PAR-2 is activated by trypsin or tryptase but not activated by thrombin.

PAR-2 is known to be activated by a tissue factor/factor VIIa, factor Xa, acrosin (a type of sperm protease) and trypsin-like serine protease identified in rat brain further to trypsin and tryptase (Pharmacological Rev. 53, 245-282, 2001, Br. J. Pharmacol. 1998, 123, 1434-1440), and it is reported that PAR-2 activation is useful in preventing and treating reduced salivary secretion, reduced lacrimal secretion and alimentary diseases (Japanese Patent Application Laid-open No. 2001-064203, Japanese Patent Application Laid-open No. 2001-181208, Japanese Patent Application Laid-open No. 2001-233790, US Patent Publication No. 5888529, and US Patent Publication No.5958407).

In biochemical experiments, the peptides mainly composed of 6 amino acids, such as Ser-Leu-Ile-Gly-Lys-Val (SEQ ID: NO: 1) -OH, Ser-Leu-Ile-Gly-Lys-Val (SEQ ID: NO: 1) -$NH_2$, Ser-Leu-Ile-Gly-Arg-Leu (SEQ ID: NO: 2) -OH, or Ser-Leu-Ile-Gly-Arg-Leu (SEQ ID: NO: 2) -$NH_2$ having the same sequence as Par-2 ligand (Tethered receptor agonist peptide :TRAP) are widely used as a PAR-2 activator; however, it is significant to obtain a compound having a simpler structure considering usefulness in the development of pharmaceutical preparation. An example of low molecular PAR-2 agonists heretofore reported is $N_\alpha$-benzoyl-Arg ($NO_2$)-Leu-$NH_2$, and intensity of this compound to activate PAR-2 is about $1/100$ of TRAP (Bioorg. Med. Chem. Lett. 2002, 12, 21-24). A compound having acyl group such as 2-furoyl substituted for an amino acid at N-terminus of TRAP is reported as PAR-2 activating agent (WO 03/104268); however, it is desired to obtain a compound having a more simplified structure. A method for reducing the number of amino acid composing the peptide is assumed as one of the methods to simplify the structure of TRAP. A peptide composed of 5 to 7 amino acids is claimed as PAR-2 activating agent in WO 96/23225 (US Patent Publication No. 5763575, [US Patent Publication No. 5874400]' COR Therapeutics Inc.], and for a peptide composed of 5 amino acids ($AA^1$—$AA^2$—$AA^3$—$AA^4$—$AA^5$), each amino acid is defined as $AA^1$: small amino acid or threonine, $AA^2$ and $AA^3$: neutral/nonpolar/large/non-aromatic amino acid, $AA^4$: small amino acid, $AA^5$: basic amino acid. Even the amino acids are specified according to its property as above, simply reducing the number of 6 amino acids composing the peptide usually results in decreased PAR-2 activation (Pharmacol.Rev.2001, 53, 245-282, J. Pharmacol. Exp. Ther. 1999, 290, 753-760, Mol. Pharmacol. 1996. 49, 229-233). However, there are considerable difficulties in industrial production of peptides composed of 6 amino acids; therefore, it has been desired to develop shorter agonist peptides having equal or higher ability of activation.

DISCLOSURE OF INVENTION

Accordingly, the object of the present invention is to provide a PAR-2 agonist retaining comparable ability to activate PAR-2 to that of TRAP or with the ability improved even with reducing the number of amino acid composing the peptide. That is, the object of the present invention is to provide a PAR-2 agonist useful for development of a pharmaceutical preparation as well as prevention of development or progress, amelioration, and treatment of conditions relating to PAR-2, such as fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

In view of the circumstances described above, the present inventors made extensive study, and as a result they found that a compound represented by the general formula (1):
General formula 1

$$A_r\text{—CO—}AA_1\text{—}AA_2\text{—}AA_3\text{—}AA_4\text{—NH—X—Y} \tag{1}$$

or salt thereof or solvate thereof have dramatically improved ability to activate PAR-2 compared to TRAP in spite of reducing the number of amino acid composing the peptide, and completed the present invention.

Within the general formula(1):
Ar represents a phenyl group or an aromatic heterocyclic group optionally having substituent(s);
$AA_1$ represents a hydrophobic amino acid;
$AA_2$ represents an amino acid absent of substituent(s) comprising more than two carbon atoms;
$AA_3$ represents an amino acid absent of substituent(s) comprising more than two carbon atoms;
$AA_4$ represents a basic amino acid;
X represents a straight chain or branched bivalent saturated aliphatic hydrocarbon group having 1 to 6 carbon atoms;
—Y represents basic substituent(s); straight, branched, or cyclic saturated aliphatic hydrocarbon group having 1 to 6 carbon atoms; or aromatic hydrocarbon group having 6 to 10 carbon atoms.

Accordingly, the present invention provides the compound represented by the above-described general formula (1), salt thereof or solvate thereof.

The present invention also relates to a pharmaceutical composition comprising a compound represented by the general formula (1) of the above, salt thereof, or solvate thereof, and pharmaceutically acceptable carrier for preventing and/or treating conditions associated with PAR-2.

The present invention further relates to a pharmaceutical composition comprising a compound represented by the general formula (1) of the above, salt thereof, or solvate thereof, and pharmaceutically acceptable carrier for preventing/treating fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

The present invention further relates to a method for preventing/treating conditions associated with PAR-2, comprising administrating an effective amount of a compound represented by the general formula (1) of the above, salt thereof, or solvate thereof, and pharmaceutically acceptable carrier to a patient susceptible to or suffering from a condition associated with PAR-2.

The present invention further relates to a method for preventing/treating fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure, comprising administrating an effective amount of a compound represented by the general formula (1) of the above, salt thereof, or solvate thereof, and pharmaceutically acceptable carrier to a patient susceptible to or suffering from the forementioned conditions.

The present invention further relates to the use of the compound (1) of the present invention, salt thereof or solvate thereof for producing a pharmaceutical composition for preventing/treating conditions associated with PAR-2.

The present invention further relates to the use of the compound (1) of the present invention, salt thereof or solvate thereof for producing a pharmaceutical composition for preventing/treating fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

According to the present invention, PAR-2 agonist which can be an effective agent for preventing/treating various conditions associated with PAR-2 can be provided. Consequently, the present invention relates to the use of the compound represented by the compound (1) of the present invention, salt thereof or solvate thereof as PAR-2 agonist.

The present invention further relates to the use of the compound represented by the compound (1) of the present invention, salt thereof or solvate thereof as an active ingredient in a pharmaceutical composition for preventing/treating fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

BEST MODE FOR CARRYING OUT THE INVENTION $A_r$ in the general formula (1) represents a phenyl group or an aromatic heterocyclic group optionally having substituent (s), preferably an aromatic heterocyclic group optionally having substituent (s). The aromatic heterocyclic group of the present invention is a monocyclic, polycyclic or condensed cyclic group comprising 5- to 7-membered aromatic heterocyclic ring wherein the aromatic heterocyclic ring has one or more than two heteroatom(s) selected from a group consisting of nitrogen, oxygen or sulfur within at least one ring. The preferable aromatic heterocyclic group is, for example, furyl group, pyridyl group, benzofuryl group, isoxazoryl group, or imidazolyl group, particularly furyl group.

The phenyl group and aromatic heterocyclic group mentioned above can be with/without substituent (s). Examples of the substituent (s) are a straight chain or branched alkyl group having 1 to 8 carbon atoms, preferably 1 to 6, more preferably 1 to 3 carbon atoms, such as a methyl group, ethyl group or n-propyl group; an al koxy group composed of a straight chain or branched alkyl group having 1 to 8 carbon atoms, preferably 1 to 6, more preferably 1 to 3 carbon atoms, such as a methoxy group or ethoxy group; a halogen atom such as bromine atom and chlorine atom. Examples of preferable substituted aromatic heterocyclic groups are a bromofuryl group, dimethylfuryl group, etc.

—$Alk_1$—$AA_2$—$AA_3$—$AA_4$— of the general formula (1) represents a peptide composed of 4 amino acids by notation for peptides, wherein the left end represents N-terminal and the right end represents C-terminal. Each $AA_1$—$AA_2$—$AA_3$, and $AA_4$ shows amino acids composing the peptide composed of 4 amino acids.

A hydrophobic amino acid, an amino acid absent of substituent (s) comprising more than two carbon atoms, and a basic amino acid of the present invention can be an a-amino acid whose carboxyl group has amino group attached at the a position, and can be either natural or unnatural. When such amino acids are optically active, they can be D-isomer, L-isomer or racemate, however L-amino acid is usually preferred.

The amino acid represented by $AA_1$ is a hydrophobic amino acid, which is, for example, an amino acid substituted with a saturated or unsaturated straight chain, branched or cyclic hydrocarbon group having 2 to 20 carbon atoms, preferably 2 to 10, more preferably 3 to 10 carbon atoms, at the a position. Examples of the hydrocarbon group are straight chain or branched alkyl group having 2 to 8 carbon atoms, preferably 2 to 6, more preferably 3 to 6 carbon atoms, such as isopropyl group, 2-methylpropyl group and 1-methyl-propyl group; saturated cycloaliphatic hydrocarbon group having 5 to 20 carbon atoms, preferably 5 to 10, more preferably 6 to 10 carbon atoms, such as cyclohexylmethyl group and cyclohexylethyl group;

or aromatic aliphatic group (aralkyl group) having 7 to 20 carbon atoms, preferably 7 to 12, more preferably 7 to 10 carbon atoms, such as benzyl group. Examples of preferable amino acid of $AA_1$ are β-cyclohexylalanine, phenylalanine, isoleucine, leucine, valine, more preferably β-cyclohexylalanine.

$AA_2$ represents an amino acid absent of substituent(s) having more than two carbon atoms, preferably an amino acid absent of substituent(s) comprising more than one carbon atom. That is, $AA_2$ represents an amino acid whose carbon chain between the carboxyl group and the amino group is absent of substituent(s), or an amino acid having one or more hydrogen atom substituted with substituent(s) composing 0 or 1 carbon atom. Examples of a substituent comprising one carbon atom are methyl group, chloromethyl group, fluoromethyl group, difluoromethyl group and trifluoromethyl group, and a substituent composing 0 carbon atom is, for example, halogen atoms such as chlorine atom and fluorine atom. Examples of preferable amino acid for $AA_2$ are glycine such as glycine, α-fluoroglycine or α,α-difluoroglycine, and glycine derivatives such as halogenated glycines; however, glycine is more preferable.

$AA_3$ represents an amino acid absent of substituent(s) having more than two carbon atoms, preferably an amino acid absent of substituent(s) comprising more than one carbon atom. That is, $AA_3$ represents an amino acid whose carbon chain between the carboxyl group and the amino group is absent of substituent(s), or an amino acid having one or more hydrogen atom substituted with substituent(s) composing 0 or 1 carbon atom. Examples of a substituent comprising one carbon atom are methyl group, chloromethyl group, fluoromethyl group, difluoromethyl group and trifluoromethyl group, and a substituent composing 0 carbon atom is, for example, halogen atoms such as chlorine atom and fluorine atom. Examples of preferable amino acid for $AA_3$ are glycine such as glycine, α-fluoroglycine or α,α-difluoroglycine, and glycine derivatives such as halogenated glycines; however, glycine is more preferable.

The basic amino acid represented by $AA_4$ refers to an amino acid which is substituted with one or two straight chain or branched saturated or unsaturated aliphatic hydrocarbon group having 1 to 10 carbon atoms, preferably 1 to 6 carbon atoms, having one or more than two basic substituent(s) such as amino group, substituted amino group, amidino group, guanidino group, cyclic amino group. The basic substituent group herein is, for example, amino group; monoalkylamino group such as methyl amino group and ethylamino group; dialkylamino group such as dimethylamino group and diethylamino group; cyclic amino group such as pyrrolidinyl group, piperidinyl group, morpholino group, piperazinyl group, alkylpiperazinyl group, homopiperazinyl group, alkylhomopiperazinyl group, pyridyl group, imidazolyl group and alkylimidazolyl group; amidino group, guadinino group and the like. Alkyl group as a substituent in monoalkylamino group, dialkylamino group, alkylpiperazinyl group, alkylhomopiperazinyl group, or alkylimidazolyl group is, for example, alkyl group with 1 to 10 carbon atoms selected from a group consisting of straight chain or branched alkyl group having 1 to 10, preferably 1 to 6 carbon atoms, and saturated cyclo alkyl group (cycloalkyl group) having 3 to 10, preferably 3 to 6 carbon atoms. Preferable alkyl group are, for example, methyl group, ethyl group, n-propyl group, n-butyl group, n-pentyl group, n-hexyl group, isopropyl group, isobutyl group, sec-butyl group, cyclopropyl group, cyclobutyl group, cyclopentyl group, cyclohexyl group. Also, a straight chain or branched saturated or unsaturated aliphatic hydrocarbon group with 1 to 10, preferably 1 to 6 carbon atoms is, for example, alkyl group or alkenyl group, preferably alkyl group such as methyl group, ethyl group, n-propyl group, n-butyl group, n-pentyl group and n-hexyl group. Examples of preferable basic amino acid are α amino acid substituted with methyl group, ethyl group, n-propyl group, n-butyl group, n-pentyl group and n-hexyl group having piperidinyl group at the α position, particularly α amino acid substituted with n-propyl group having piperidinyl group at the α position is preferable, and α-[3-(1-piperidinyl)propyl]glycine is the most preferable.

X shown in the general formula (1) is, for example, a straight chain or branched bivalent saturated aliphatic hydrocarbon group having 1 to 6 carbon atoms, preferably 1 to 4, more preferably 1 to 3 carbon atoms, and preferably a straight chain group represented by the following formula:

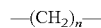

$$-(CH_2)_n-$$

wherein, n represents a whole number 1 to 6.

The bivalent saturated aliphatic hydrocarbon group is, for example, methylene group, ethylene group, propylene group, butylene group. Examples of preferable bivalent saturated aliphatic hydrocarbon group are methylene group and ethylene group.

Y shown in the general formula (1) represents basic substituent (s); straight, branched, or cyclic saturated aliphatic hydrocarbon group having 1 to 6 carbon atoms; or aromatic hydrocarbon group having 6 to 10 carbon atoms. The basic substituent means the basic substituent as described above, which is amino group, monoalkylamino group, dialkylamino group, pyrrolidinyl group, piperidinyl group, morpholino group, piperazinyl group, alkylpiperazinyl group, homopiperazinyl group, alkylhomopiperazinyl group, pyridyl group, imidazolyl group, alkylimidazolyl group, amidino group, guadinino group and the like, preferably dialkylamino group, pyrrolidinyl group, piperidinyl group, morpholino group, alkylpiperazinyl group, alkylhomopiperazinyl group, pyridyl group. For alkyl group in monoalkylamino group, dialkylamino group, alkylpiperazinyl group, alkylhomopiperazinyl group, or alkylimidazolyl group herein is, for example, an alkyl group having 1 to 10 carbon atoms selected from a group consisting of straight chain or branched alkyl group having 1 to 10, preferably 1 to 6 carbon atoms, and saturated cyclo alkyl group (cycloalkyl group) having 3 to 10, preferably 3 to 6 carbon atoms; and the preferable alkyl group is, for example, methyl group, ethyl group, n-propyl group, n-butyl group, n-pentyl group, n-hexyl group, isopropyl group, isobutyl group, sec-butyl group, cyclopropyl group, cyclobutyl group, cyclopentyl group, cyclohexyl group.

A straight, branched, or cyclic saturated aliphatic hydrocarbon group having 1 to 6 carbon atoms represented by Y is hydrocarbon group selected from a group consisting of straight chain or branched alkyl group having 1 to 6 carbon atoms, and saturated cyclo alkyl group (cycloalkyl group) having 3 to 6 carbon atoms; for example, methyl group, ethyl group, n-propyl group, n-butyl group, n-pentyl group, n-hexyl group, isopropyl group, isobutyl group, sec-butyl group, cyclopropyl group, cyclobutyl group, cyclopentyl group, cyclohexyl group, preferably cyclopentyl group and cyclohexyl group.

Also, an aromatic hydrocarbon group having 6 to 10 carbon atoms represented by Y is monocyclic, polycyclic, or condensed-cyclic hydrocarbon group having at least one 6-membered aromatic ring; for example, phenyl group, indenyl group, dihydroindenyl group, naphthyl group and tetrahydro naphthyl group, and preferable aromatic hydrocarbon group is, for example, phenyl group or naphthyl group. Examples of particularly preferable group represented by Y are piperidinyl group and phenyl group.

A salt of the compound represented by the general formula (1) is, but not limited to insofar as pharmaceutically acceptable salt, preferably an acid addition salt, for example, mineral acid addition salt such as hydrochloride, hydrobromide, hydroiodide, sulfate and phosphate; and organic acid addition salt such as benzoate, methanesulfonate, ethanesulfonate, benzenesulfonate, p-toluenesulfonate, oxalate, maleate, fumarate, tartrate, citrate and acetate.

Further, when the compound represented by the general formula (1) is in the form of solvate such as hydrate, the solvate can be comprised in the compound. Further, when the compound represented by the general formula (1) has one or more of asymmetric carbon atoms, the present invention also includes any configurational isomers.

The PAR-2 activation of peptide derivatives represented by the general formula (1) can be tested by various known methods. For example, the method of Hollenberg (Hollenberg, M.D., et al., Can. J. Physiol. Pharmacol., 75, 832-841(1997)), the method of Kawabata et al. (Kawabata, A., et al., J. Pharmacol. Exp. Ther., 288, 358-370(1999)), the method of Howthorne et al. (Howthorne et al., A High-Throughput Microtiter Plate-Based Calcium Assay for the Study of Protease-Activated Receptor 2 Activation, Analytical Biochemistry 290, 378-379(2001)), and the like can be used. The present inventors tested PAR-2 activation potency by using the modified method of Howthorne et al. More specifically the method is for assaying calcium dynamics in a cell expressing human PAR-2 intracellularly. In this assay, PAR-2 agonist mediated calcium dynamics (concentration variability) in a cell is measured by using a multiple-well plate reader wherein the cell has $Ca^{2+}$ sensitive fluorescent dye introduced and stimulated by PAR-2 agonist under probenecid, which inhibits anion-exchange transporter, present.

The method is described below in more detail.

HCT-15 cells, human colorectal cancer cell lines endogenously expressing high level of PAR-2, were plated in a black-wall clear-bottom 96 well plate. Subconfluent cells were labeled with $Ca^{2+}$ sensitive fluorescent dye (Calcium Assay Reagent, Molecular Devices) in a RPMI culture medium in the presence of 2.5 mM probenecid absence of serum, and incubated for 1 hour at 37° C. Thereafter, the cells were stimulated with test compounds at various concentrations, and fluorescence change was measured using a scanning fluorometer (Flex Station, Molecular Devices) using excitation wavelength of 485 nm and fluorescence wavelength of 525 nm (cut-off wavelength of 515 nm). As a comparative compound, SLIGKV(SEQ ID: NO 1)—OH which is known as PAR-2 activated peptide was used. The results are shown in TAB.1.

[TAB. 1]

| Compound (Example No.) | MW (Calculated value) | Agonist activity (EC50, μM) |
|---|---|---|
| Comparison compound (SLIGKV(SEQ ID: NO 1)—OH) | — | 15.6 ± 0.9 |
| Example 1 | 650.81 | 2.3 ± 0.3 |
| Example 2 | 744.79 | 4.1 ± 0.4 |

As a result, both compounds of example 1 and example 2 showed higher agonist activity against PAR-2

A compound represented by the general formula (1) below can be synthesized by forming five amide-linkages in the molecule by amidation between an appropriate carboxylic acid and an appropriate amine in arbitrary order. It is possible to introduce an amide-linkage at the N-terminus and C-terminus after producing peptide portion according to a conventional method of peptide synthesis; however, in an example of preferable synthetic method, a dipeptide $AA_2$—$AA_3$ is synthesized initially, followed by connection with $AA_1$ to form a peptide H—$AA_1$—$AA_2$—$AA_3$—OH, which is protected as necessary, then the amino group of the N-terminus is acylated to provide N-acylated peptide represented by a general formula (2):

$$Ar—CO—AA^1—AA^2—AA^3—OH \quad (2)$$

wherein, $A_r$, $AA_1$, $AA_2$, and $AA_3$ represent the same as the above-mentioned; the peptide is then reacted with an amino acid derivative represented by a general formula (3):

$$H—AA_4—NH—X—Y \quad (3)$$

wherein, $AA_4$ and $R_1$ represent the same as the above-mentioned, to obtain a compound represented by the general formula (1). Amino acid derivatives represented by the general formula (3) above can be produced preferably by reacting an amino acid $AA_4$ whose amino group is protected with an amine $NH_2$-$R_1$.

For such an N-acylation reaction and an amidation reaction, various amidation methods used for conventional peptide synthesis are applicable. Various methods such as solid-phase methods and solution-phase methods can also be used.

For amidation in the present invention, a method used in a peptide synthesis such as activated ester method and anhydride method can be used arbitrarily, preferably a method using a condensation reagent and a method using a reactive derivative of the compound having a carboxyl group. Examples of the condensation reagent in the amidation are 1,3-dicyclohexylcarbodiimide, 1-cyclohexyl-3-morpholino-ethylcarbodiimide, 1-(3-diaminopropyl)-3-ethylcarbodiim-ide, 1,1'-carbonyldiimidazole, diethylphosphoryl cyanide, diphenylphosphoryl azide, bis(2-oxo-3-oxazolidinyl)phosphinic chloride, 2-chloro-l-methylpyridinium iodide, and the like. Examples of the reactive derivatives of the compound having a carboxyl group are an acyl halide such as acid chloride, acid azide, symmetric anhydride, or mixed anhydride formed with, for example, pivalic acid, an activated ester such as p-nitrophenyl ester and the like. If necessary, an appropriate base or appropriate solvent can be used when these reactions are carried out. Examples of the bases are an organic bases such as pyridine, triethylamine, and N,N-diisopropylethylamine; or an inorganic base such as sodium carbonate, and sodium hydrogencarbonate. Examples of the solvent are such as N,N-dimethylformamide, tetrahydrofuran, 1,4-dioxane, acetonitrile, methylene chloride, and 1, 2-dichroloethane . Further, when a condensation reagent such as 1,3-dicyclohexylcarbodiimide is used, it is effective to add an appropriate activating agent such as 1-hydroxybenzotriazole and N-hydroxysuccinimide to accelerate the reaction and to inhibit racemization. Further, to simplify an isolation operation of the synthesized peptide, various reagents listed here can be modified for a solid-phase by binding on a resin such as polystyrene.

In the process of synthesizing the compound represented by the general formula (1), functional groups present in starting materials and intermediates that should not engage with the expected reaction, can be protected and deprotected in order to inhibit unfavorable side reactions. For the protection and deprotection, a conventional method used in a peptide synthesis can be applied. For example, as the protected carboxyl group, methyl ester, ethyl ester, t-butyl ester, and benzyl ester can be used; and as the protected amino group, methyl carbamate, allyl carbamate, t-butyl carbamate, benzyl carbamate, 9-fluorenylmethyl carbamate, p-methoxybenzyl carbamate, a formamide, acetamide, 3-nitro-2-pyridinesulfenamide, phthalimide can be used. These protecting groups can be removed by acid treatment, base treatment, reduction, hydrolysis and the like according to the properties of the protecting groups. The acid used in these methods is hydrogen chloride, hydrogen fluoride, methanesulfonic acid, trifluoromethanesulfonic acid, trifluoroacetic acid, trimethylsilyl bromide, trimethylsilyl trifluoromethanesulfonate, tetrafuloroboric acid, boron tribromide and the like; and the base is piperidine, pyrrolidine, triethylamine, N,N-diisopropylethylamine and the like. Further, for reductive condition, sodium/liquid ammonia, palladium catalyst/hydrogen, palladium catalyst/formic acid and the like can be used; and for hydrolysis condition, lithium hydroxide, sodium hydroxide and the like can be used.

The compound relating to the present invention obtained by the above method can be purified in need by the usual method, for example, gel chromatography, partition chromatography, ion-exchange chromatography, affinity chromatography, countercurrent chromatography, high-performance liquid chromatography with various absorbents, or recrystallization and the like. The compound can also be obtained in the form of a salt or solvate expected as above according to the usual manner. The more specific examples of the method producing the compound represented by the general formula (1) are described in more detail with reference to the Examples.

The pharmaceutical composition of the present invention contains the compound represented by the general formula (1), salt thereof and solvate thereof as the active ingredient, and the administration route includes, but not limited to, for example an oral agent, an injection, a suppository, an ointment, an inhalant, eye drops, nasal drops, and an adhesive preparation, and any of these can be selected according to the therapeutic purpose. A pharmaceutical composition suitable for each administration route comprise a pharmaceutically acceptable carrier and can be manufactured according to a method known to those skilled in the art.

In preparing an oral solid preparation, add excipients; and a binder, a disintegrating agent, a lubricant, a coloring agent, a flavoring substance, a fragrant substance and the like in need, to the compound represented by the general formula (1) of the present invention, and then produce tablets, coated tablets, granules, powder, capsules or the like in a usual manner. Such additives may be those generally used in the art; for example, the excipients include lactose, sucrose, sodium chloride, glucose, starch, calcium carbonate, kaolin, microcrystalline cellulose, silicic acid and the like, the binder includes water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like; the disintegrating agent includes dry starch, sodium alginate, powdered agar, sodium hydrogen carbonate, calcium carbonate, sodium lauryl sulfate, stearic acid monoglyceride, lactose and the like, the lubricant includes purified talc, stearate, borax, polyethylene glycol and the like; and the flavoring substance includes sucrose, wild orange peel, citric acid, tartaric acid and the like.

In preparing an oral liquid preparation, add a flavoring substance, a buffer agent, a stabilizer, a fragrant substance and the like to the compound represented by the general formula (1), to produce an oral liquid for internal use, syrup, elixir and the like in a usual manner. Here the flavoring substance may be the one described above; the buffer agent includes sodium citrate and the like; and the stabilizer includes tragacanth, gum arabic, gelatin and the like.

In preparing an injection, add pH adjusting agent, a buffer agent, a stabilizer, a tonicity agent, a topical anesthetic agent or the like to the compound represented by the general formula (1), to produce subcutaneous, intramuscular and intravascular injections in a usual manner. Here the pH adjusting agent and the buffer agent include sodium citrate, sodium acetate, sodium phosphate and the like. The stabilizer includes sodiumpyrosulfite, EDTA, thioglycolic acid, thiolactic acid and the like. The topical anesthetic agent includes procaine hydrochloride, lidocaine hydrochloride and the like. The tonicity agent can be exemplified by sodium chloride, glucose and the like.

In preparing a suppository, add pharmaceutical carriers known in the art, such as polyethylene glycol, lanolin, cacao seed oil, fatty acid triglyceride and the like, and add a surfactant such as Tween (registered trademark) in need, and then produce a suppository in a usual manner.

In preparing an ointment, add additives usually used such as a base, a stabilizer, a moistening agent and a preservative to the compound represented by the general formula (1) in need, blend them in a usual manner to produce an ointment. The base includes liquid paraffin, white petrolatum, Sarashi beeswax, octyldodecyl alcohol, paraffin and the like. The preservative includes methyl p-hydroxybenzoate, ethyl p-hydroxybenzoate, propyl p-hydroxybenzoate, and the like.

In addition to those described above, an inhalant, eye drops and nasal drops can also be prepared in a usual manner.

The amount of the active ingredient in the pharmaceutical composition of the present invention to be administered varies depending on such as the age, sex, weight and symptoms of the patient, therapeutic effect, treatment time, administration form, and administration frequency, but usually the compound (1) of the present invention is administered to an adult orally or parenterally in the range of 0.001 to 1000 mg, preferably 0.01 mg to 500 mg, more preferably 0.1 mg to 100 mg all at once or in divided portions per day. However, the dose varies depending on various conditions, and thus a dose lower than the above may be sufficient in some cases or a dose higher than the above range may be necessary in other cases. For example, the injection can be produced by dissolving or suspending the compound represented by the general formula (1) of the present invention at a concentration of 0.1 µg/mL to 10 mg/mL in a nontoxic pharmaceutically acceptable carrier such as physiological saline or commercial distilled water for injection.

The injection thus obtained can be administered in a dose of 1 μg to 100 mg, preferably 50 μg to 50 mg, for each administration, per body kg once to several times per day to a patient in need of treatment. The administration route can be exemplified by medically suitable administration route such as intravenous injection, subcutaneous injection, intradermal injection, intramuscular injection and intraperitoneal injection, preferably intravenous injection. The injection can also be prepared as a suspension or emulsion with a non-aqueous diluent (for example, propylene glycol, polyethylene glycol and vegetable oils such as olive oil and alcohols such as ethanol) depending on the case. Sterilization of such injections can be carried out by filter sterilization, that is, through a bacteria-retaining filter, or with a sterilizer or through γ-ray irradiation. The injection can be produced in a form for preparation just before use. That is, a germ-free solid composition is produced by lyophilization and can be dissolved in germ-free distilled water for injection or other solvent just before use.

The thus obtained compound represented by the general formula (1) of the present invention has PAR-2 agonist action as shown later in the Test Examples; therefore, the compound can be used as PAR-2 agonist. Further, the compound is useful for prevention of development or progress, amelioration, and treatment of PAR-2 associated conditions, for example, fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

Further, the compound represented by the general formula (1) is also useful for prevention of development or progress, amelioration, and treatment of fever (rheumatic fever and influenza and other viral infection-related fever), common cold, dysmenorrheal, menstrual cramp, Crohn's disease, emphysema, acute respiratory distress syndrome, transplant toxic potency, dyscrasia, tissue ulcer, peptic ulcer, gastritis, diverticulitis, recurrent gastrointestinal lesion, gastrointestinal bleeding, blood coagulation, anemia, gout, ankylosing spondylitis, restenosis, periodontal disease, skin fragility, osteoporosis, prosthesis implant loosening, aortic aneurysm (abdominal aortic aneurysm and cerebral aortic aneurysm), periarteritis nodosa, congestive heart failure, spasm, head injury, spinal cord injury, neurogenerative disease (acute neurogenerating disease and chronic neurogenerating disease), Huntington's disease, Parkinson's disease, migraine headache, depression, peripheral neuropathy, gingivitis, cerebral amyloid angiopathy, nootropic or recognition enhancement, amyotrophic lateral sclerosis, multiple sclerosis, corneal injury, yellow spot degeneration, tendinitis, myasthenia gravis, polymyositis, myositis, bursitis, burn, diabetes mellitus(types I and type II diabetes mellitus, diabetic retinopathy), tumor invasion, tumor growth, tumor metastasis, corneal scar, scleritis, immunodeficiency disorders(for example, human AIDS and feline AIDS), sepsis, preterm delivery, hypoprothrombinemia, hemophila, thyroiditis, sarcoidosis, Bechet's syndrome, anaphylaxis , kidney disorders and the like.

EXAMPLES

Hereinafter, the present invention is described in more detail by reference to the Examples, but the technical scope of the present invention is not limited to the Examples.

Reference Example 1

Production of 2-furoyl-β-cyclohexyl-L-alanyl-glycyl-glycine 2-furoyl-β-cyclohexyl-L-alanyl-glycyl-glycine represented by the formula:

[Chemical formula 1]

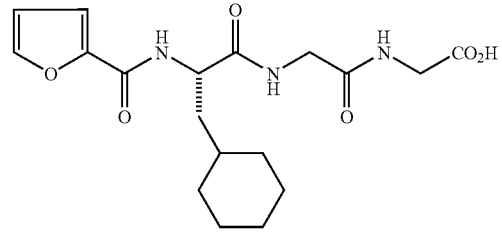

is produced according to the following method.

To a solution of 289.4mg (1.47 mmol) of glycyl-glycine ethyl ester hydrochloride in anhydrous tetrahydrofuran (5 mL), 155.9 mg(1.54 mmol) of triethylamine, 451.5 mg (1.47 mmol) of N-t-butoxycarbonyl-β-cyclohexyl-L-alanine dihydrate, 205.3 mg (1.52 mmol) of 1-hydroxybenzotriazole hydrate, and 292.7 mg (1.53 mmol) of 1-[3-(dimethylaminomethyl)propyl]-3-ethylcarbodiimide hydrochloride were added sequentially with stirring under ice cooling. After the mixture was stirred for 1 hour, the reaction mixture was stirred at room temperature for 0.5 hour. The reaction mixture was concentrated under reduced pressure, chloroform (30 mL) was added to the residues, and the solution was washed sequentially with 0.5M hydrochloric acid (3×5 mL), water (3×5 mL) and 5% aqueous sodium hydrogencarbonate solution (3 ×5 mL). The organic layer was dried over anhydrous sodium sulfate and concentrated under reduced pressure , whereby 570 mg of a crude product was obtained. The crude product was purified by column chromatography on alumina (alumina 2 g, chloroform), to give 552.8 mg of N-t-butoxycarbonyl-β-cyclohexyl-L-alanyl-glycyl-glycine ethyl ester (yield 91%) as a colorless crystalline powder.

To the solution of thus obtained N-t-butoxycarbonyl-β-cyclohexyl-L-alanyl-glycyl-glycine ethy lester (506.2 mg, 1.22 mmol) in ethyl acetate (1 mL) under ice-cold condition, add 4M hydrogen chloride/ethyl acetate (3.0 mL, 12 mmol) with stirring, and then the reaction mixture was stirred for 4.5 hours at room temperature. Diethylether (12 mL) was added and the mixture was stirred under ice-cold condition, then the precipitate was collected by filtration to obtain hygroscopic crude crystals. The crude crystals were suspended in diethylether (10 mL)and collected by filtration to obtain β-cyclohexyl-L-alanyl-glycyl-glycine ethyl ester hydrochloride (370.3 mg) as colorless crystalline powder (yield 86%).

To a solution of thus obtained β-cyclohexyl-L-alanyl-glycyl-glycine ethyl ester hydrochloride (90.1 mg, 0.258 mmol) in methylene chloride (1 mL) with stirring under ice cooling, N,N-diisopropylethylamine (100.0 mg, 0.774 mmol) and 2-furoyl chloride(37.2 mg, 0.285 mmol) were added and the reaction mixture was stirred for 0.5 hour. After addition of methanol (0.2 mL), the reaction mixture was stirred under room temperature and concentrated under vacuum. To the residue, chloroform (25 mL) was added and the solution was washed with 0.5 M hydrochloric acid (3×5 mL) and 5% aqueous sodium hydrogen carbonate solution (3×5 mL). The organic phase was dried over anhydrous sodium sulfate and concentrated under vacuum to obtain a crude product (127 mg). The crude product was purified by silica-gel column chromatography [silica gel 7.5 g, chloroform ->methanol-chloroform (1:100)] to obtain 2-furoyl-β-cyclohexyl-L-alanyl-glycyl-glycine ethyl ester (103.2 mg) as a colorless oily material (yield 98%).

To the solution of the resulting 2-furoyl-β-cyclohexyl-L-alanyl-glycyl-glycine ethyl ester (22.5 mg, 0.0552 mmol) in tetrahydrofuran (0.2 mL), were added water (0.1 mL) and lithium hydroxide monohydrate (2.7 mg, 0.0643 mmol). After stirring for 1 hour at room temperature, were added water-ethanol (1:10, 0.5 mL) and weakly acidic ion-exchange resin (Amberlite™ IRC-50 H*) (48.1 mg; about 0.48 mg equivalent), and the mixture was stirred for 0.5 hour. IRC-50 (0.3 mg) was swelled in water-ethanol (1:10) and filled in a glass tube, and the mixture was loaded on, then the column was eluted with water-ethanol (1:10, 7.5 mL). The eluted solution was concentrated under vacuum to obtain the title compound (20.3 mg) as a colorless oily material.

Reference Example 2

Production of (S)-2-amino-5-(1-piperidinyl)pentanoic Acid Benzyl Amide (S)-2-amino-5-(1-piperidinyl)pentanoic acid benzyl amide represented by the formula:

[Chemical formula 2]

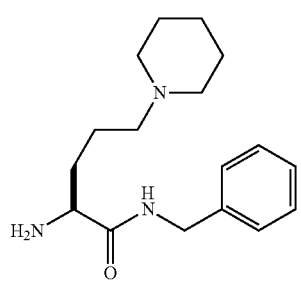

is produced according to the following method.

To a solution of N-t-butoxycarbonyl-(S)-2-amino-5-iodopentanoic acid benzyl ester(J.Org. Chem. 1998, 7875-7884) (100.8 mg, 0.23 mmol) in N,N-dimethylformamide (0.25 mL) was added piperidine (41.5 mg, 0.49 mmol) and the mixture was stirred for 3 hours at room temperature. To the reaction mixture was added chloroform (30 mL) and the mixture was washed with saturated aqueous sodium hydrogencarbonate solution (3×3 mL). The organic phase was dried over anhydrous sodium sulfate and concentrated under vacuum to obtain crude N-t-butoxycarbonyl-(S)-2-amino-5-(1-piperidinyl)pentanoic acid benzyl ester(83.8 mg) as a colorless oily material.

To a solution of crude N-t-butoxycarbonyl-(S)-2-amino-5-(1-piperidinyl)pentanoic acid benzyl ester in ethanol (1.5 mL) was added 5% palladium-carbon (15.0 mg) and the mixture was stirred for 1 hour under hydrogen atmosphere. The insoluble materials were removed by suction filtration using selite, and the residue was washed with ethanol (10 mL). The filtrate and washings were collected and concentrated under vacuum to obtain crude N-t-butoxycarbonyl-(S)-2-amino-5-(1-piperidinyl)pentanoic acid (69.0 mg) as a colorless oily material.

To a solution of crude N-t-butoxycarbonyl-(S)-2-amino-5-(1-piperidinyl)pentanoic acid (22.2 mg, 0.074 mmol) in anhydrous methylene chloride (0.50 mL) were added benzyl amine (9.7 mg, 0.091 mmmol) and 1-hydroxybenzotriazol monohydrate (11.1 mg, 0.082 mmol). To the reaction mixture stirred under ice-cold condition was added 1,3-dicyclohexylcarbodiimide (18.0 mg, 0.087 mmol), and the mixture was stirred for 0.5 hour. After removal of the ice bath, the mixture was stirred for 16 hours at room temperature, and then chloroform (20 mL) was added. The organic phase was washed with saturated aqueous sodium hydrogencarbonate solution (2×3 mL), dried over anhydrous sodium sulfate, and concentrated under vacuum to obtain a crude oily material (47 . 7 mg). The crude oil was purified by column chromatography (silica gel 2g, about 15% ammonia/methanol-chloroform (1:100)) to obtain N-t-butoxycarbonyl-(S)-2-amino-5-(1-piperidinyl)pentanoic acid benzyl amide (26.2 mg) as a colorless oily material [yield 90% from N-t-butoxycarbonyl-(S)-2-amino-5-(1-piperidinyl)pentanoic acid benzyl ether].

To a solution of N-t-butoxycarbonyl-(S)-2-amino-5-(1-piperidinyl)pentanoic acid benzyl amide (26.2 mg, 0.067 mmol) in ethyl acetate (0.5 mL) was added 4M hydrogen chloride/ethyl acetate solution (1. 0 mL, 4 mmol), and the reaction mixture was stirred for 2 hours at room temperature. The reaction mixture was concentrated under vacuum and the residue was purified by alumina column chromatography [alumina 0.3 g, methanol-chloroform (1:4)] to obtain the title compound as a colorless oily material (yield 68%)

Example 1

Production of (S)-2-[(2-furoyl)-β-cyclohexyl-L-alanyl-glycyl-glycyl-amino]-5-(1-piperidinyl)pentanoic acid benzyl amide The title compound represented by the formula:

[Chemical formula 3]

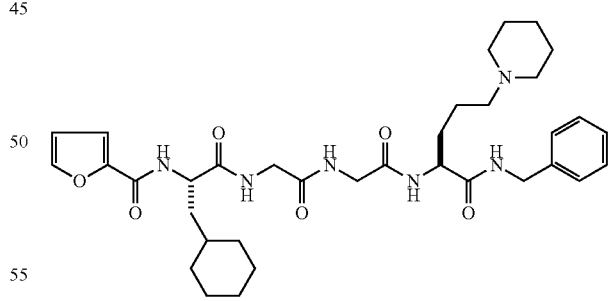

is produced according to the following method.

To a solution of the 2-furoyl-β-cyclohexyl-L-alanyl-glycyl-glycine (21.4 mg, 0.056 mmol) produced according to Reference Example 1 described above, and (S)-2-amino-5-(1-piperidinyl)-pentanoic acid benzyl amide produced according to Reference Example 2 (13.2 mg, 0.046 mmol) in anhydrous methylene chloride (0.5 mL) with stirring under ice cooling were added 1-hydroxybenzotriazole monohydrate and 1,3-dicyclohexylcarbodiimide (10.8 mg, 0.052 mmol). After stirring for 1 hour under ice-cold condition and for 12 hours at room temperature, the reaction mixture was purified by silica gel thin-layer chromatography [about 15% ammonia/methanol-chloroform (1:10)] to obtain a colorless oily material (33.8 mg). The oily material was purified by silica gel thin-layer chromatography [about 15% ammonia/methanol-chloroform-toluene (1:3:3)] to obtain the title compound (27.8 mg) as a colorless oily material (yield 94%). The colorless oily material of the title compound was recrystallized from chloroform-hexane to obtain a colorless crystalline powder (melting point 205-209° C.).

$^1$H-NMR (CDCl$_3$) δ:
7.95 (1 H, br. s), 7.86 (1 H, br. s), 7.50-7.70 (2 H, m), 7.38 (1 H, br. s), 7.20-7.30 (6 H, m), 7.03 (1 H, br. d, J=3.2 Hz), 6.42 (1 H, dd, J=3.2, 1.6 Hz), 4.58-4.75 (2 H, m), 4.47 (1 H, dd, J=15.0, 5.9 Hz), 4.37 (1 H, dd, J=15.0, 5.7 Hz), 3.91-4.12 (4 H, m), 2.24-2.41 (6 H, m), 1.45-2.00 (16 H, m), 1.30-1.45 (2 H, m), 1.06-1.29 (3 H, m), 0.84-1.01 (2 H, m).

Example 2

Production of (S)-2-[(2-furoyl)-β-cyclohexyl-L-alanyl-glycyl-glycyl-amino]-5-(1-piperidinyl)pentanoic acid N-[2-(1-piperidinyl)ethyl] amide dihydrochloride.

A compound represented by the formula:

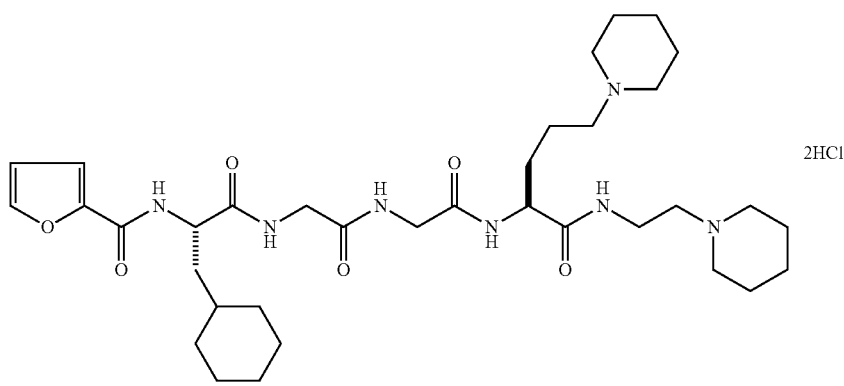

[Chemical formula 4]

is produced according to the following method.

In the same way as example 1, from 2-furoyl-L-phenylalanyl-glycyl-glycine (23.7 mg, 0.063 mmol) and (S)-2-amino-5-(1-piperidinyl)pentanoic acid N-[2-(1-piperidinyl)ethyl]amide (16.7 mg, 0.054 mmol) synthesized in the same way as reference example 1, (S)-2-[(2-furoyl)-β-cyclohexyl-L-alanyl-glycyl-glycyl-amino]-5-(1-piperidinyl)pentanoic acid [2-(1-piperidinyl)ethyl]amide (20.8 mg) was obtained as a colorless oily material (yield 58%).

To a solution of (S)-2-[(2-furoyl)-β-cyclohexyl-L-alanyl-glycyl-glycyl-amino]-5-(1-piperidinyl)pentanoic acid [2-(1-piperidinyl)ethyl]amide (20.8 mg, 0.031 mmol) in ethanol (1.0 mL), was added 1.0 M hydrochloric acid (0.10 mL, 0.10 mmol) and the mixture was concentrated under vacuum. To the residue was added ethanol (5.0 mL) and the mixture was concentrated under vacuum. Then, the residue was recrystallized from chloroform-diethylether to obtain the title compound as a colorless crystalline powder [melting point 138° C. (decomposition)]

$^1$H-NMR (CDCl$_3$) δ:
11.14 (1 H, br. s), 9.73 (1 H, br. s), 8.49 (1 H, br. s), 8.17 (1 H, br. s), 8.08 (1 H, br. d, J=7.6 Hz), 7.97 (1 H, br. s), 7.59 (1 H, br. d, J=7.6 Hz), 7.52 (1 H, br. s), 7.21 (1 H, br. d, J=3.4 Hz), 6.50 (1 H, dd, J=3.4, 1.8 Hz), 4.69-4.77 (1 H, m), 4.40 (1 H, br. ddd, J=6.8, 6.8, 6.8 Hz), 4.23 (1 H, dd, J=16.7, 6.5 Hz), 4.13 (1 H, dd, J=16.7, 7.2 Hz), 3.66-3.90 (5 H, m), 3.44-3.64 (3 H, m), 3.23 (2 H, br. s), 2.92-3.08 (2 H, m), 2.58-2.77 (4 H, m), 1.59-2.27 (21 H, m), 1.32-1.52 (3 H, m), 1.07-1.29 (3 H, m), 0.87-1.04 (2 H, m).

Industrial Applicability

The present invention provides a useful compound having PAR-2 agonist action as well as PAR-2 agonist which has improved ability of PAR-2 activation compared to TRAP in spite of reducing the number of amino acid. The present invention also provides PAR-2 agonist useful for development of a pharmaceutical preparation as well as prevention of development or progress, amelioration, and treatment of conditions such as fever, dryness of eye, corneal epithelial detachment, keratitis, corneal ulceration, conjunctival inflammation, dysfunction of masticatory, dysphagia, taste disorder, mouth odor, mouth discomfort, mouth infection, mouth inflammation, cardiovascular functional disorder, acute respiratory distress syndrome, peptic ulcer such as gastric ulceration and duodenal ulcer, gastric inflammation, visceral pain, diarrhea, enteritis such as ulcerative colitis, kidney disorder such as nephritis, pancreatitis, ulcer tissue, bone resorption, dysmenorrhea, premature labor, nephrosis, or symptom of low blood pressure.

The invention claimed is:

1. A compound represented by the general formula (1), salt thereof or solvate thereof:

$$Ar-CO-AA_1-AA_2-AA_3-AA_4-NH-X-Y \quad (1)$$

wherein Ar represents a phenyl group or an aromatic heterocyclic group optionally having substituent(s):
$AA_1$ represents a hydrophobic amino acid;
$AA_2$ represents an amino acid whose carbon chain between the carboxyl group and the amino group of the amino acid is absent of substituent(s) comprising more than two carbon atoms;
$AA_3$ represents an amino acid whose carbon chain between the carboxyl group and the amino group of the amino acid is absent of substituent(s) comprising more than two carbon atoms;
$AA_4$ represents a basic amino acid;
X represents a straight chain or branched bivalent saturated aliphatic hydrocarbon group with 1-6 carbon atoms; and
Y represents basic substituent(s); straight, branched, or cyclic saturated aliphatic hydrocarbon group having 1 to 6 carbon atoms; or aromatic hydrocarbon group having 6 to 10 carbon atoms.

2. The compound, salt or solvate according to claim 1, wherein in the general formula (1), Ar is a monocyclic, polycyclic, or condensed cyclic aromatic heterocyclic group comprising 5-7 membered aromatic heterocyclic ring having one or more of heteroatom(s) selected from the group consisting of nitrogen, oxygen and sulfur in at least one ring, and may have substituent(s) of straight chain or branched alkyl group having 1 to 8 carbon atoms, alloy group comprised of straight chain or branched alkyl group having 1 to 8 carbon atoms, or halogen atom;
$AA_1$ is an amino acid 13-cyclohexylalanine, phenylalanine, isoleucine, leucine, or valine;
$AA_2$ and $AA_3$ are identically or independently amino acids glycine, α-fluoroglycine or α,α-difluoroglycine;
$AA_4$ is an α-amino acid which is substituted at the α-position with straight chain or branched alkyl group having 1 to 6 carbon atom(s) having one or more than two types of basic substituent(s) selected from amino group, monoalkylamino group substituted with alkyl group having 1 to 10 carbon atom(s), dialkylamino group substituted with alkyl group having 1 to 10 carbon atom(s), pyrrolidinyl group, piperidinyl group, morpholino group, piperazinyl group, alkylpiperazinyl group substituted with alkyl group having 1 to 10 carbon atom(s), homopiperazinyl group, alkylhomopiperazinyl group substituted with alkyl group having 1 to 10 carbon atom(s), pyridyl group, imidazolyl group, alkylimidazolyl group substituted with alkyl group having 1 to 10 carbon atom(s), amidino group and guanidino group;
X is a straight chain-group represented by the formula:

$$-(CH_2)_n-$$

wherein, n represents a whole number 1 to 6; and
Y is a group selected from the group consisting of dialkylamino group substituted with alkyl group having 1 to 10 carbon atom(s), pyrrolidinyl group, piperidinyl group, morpholino group, alkylpiperazinyl group substituted with alkyl group having 1 to 10 carbon atom(s), alkylhomopiperazinyl group substituted with alkyl group having 1 to 10 carbon atom(s), pyridyl group, cyclopentyl group, cyclohexyl group, phenyl group and naphthyl group.

3. The compound, salt or solvate according to claim 2, wherein in the general formula (1), Ar is furyl group, pyridyl group, benzofuryl group, isoxazolyl group, imidazolyl group, bromofuryl group, or dimethylfuryl group.

4. The compound, salt or solvate according to claim 1, wherein, in the general formula (1), $A_r$ is furyl group; $AA_1$ is β-cyclohexylalanine: $AA_2$ and $AA_3$ are glycine; $AA_4$ is an α-amino acid which is substituted at the α-position with methyl group, ethyl group, n-propyl group, n-butyl group, n-pentyl group or n-hexyl group having piperidinyl group; X is methylene group or ethylene group; and Y is piperidinyl group or phenyl group.

5. The compound, salt or solvate according to claim 1, wherein a compound represented by the formula (1) is (S)-2-[(2-furoyl)-β-cyclohexyl-L-alanyl-glycyl-glycyl-amino]-5-(1-piperidinyl)pentanoic acid benzyl amide or (S)-2-[(2-furoyl)-β-cyclohexyl-L-alanyl-glycyl-glycyl-amino]-5-(1-piperidinyl)pentanoic acid[2-(1-piperidinyl)ethyl] amide.

6. A pharmaceutical composition comprising a compound, salt or solvate according to claim 1 and a pharmaceutically acceptable carrier.

7. The pharmaceutical composition according to claim 6, wherein the pharmaceutical composition is for preventing/treating conditions associated with PAR-2.

8. The pharmaceutical composition according to claim 6, wherein the pharmaceutical composition is for preventing/treating fever, dryness of eye, corneal epithelial detachment, keratitis, corneal ulceration, conjunctival inflammation, masticatory dysfunction, dysphagia, taste disorder, mouth odor, mouth discomfort, mouth infection, mouth inflammation, cardiovascular functional disorder, acute respiratory distress syndrome, peptic ulcer, gastric inflammation, visceral pain, diarrhea, enteritis, kidney disorder, pancreatitis, ulcer tissue, bone resorption, dysmenorrhea, premature labor, nephrosis, or symptom of low blood pressure.

9. A method for preventing/treating conditions associated with PAR-2, comprising administrating an effective amount of a compound, salt or solvate according to claim 1 to a patient susceptible to or suffering from a condition associated with PAR-2.

10. The method for preventing/treating conditions according to claim 9, wherein the condition associated with PAR-2 is fever, dryness of eye, corneal epithelial detachment, keratitis, corneal ulceration, conjunctival inflammation, masticatory dysfunction, dysphagia, taste disorder, mouth odor, mouth discomfort, mouth infection, mouth inflammation, cardiovascular functional disorder, acute respiratory distress syndrome, peptic ulcer, gastric inflammation, visceral pain, diarrhea, enteritis, kidney disorder, pancreatitis, ulcer tissue, bone resorption, dysmenorrhea, premature labor, nephrosis, or symptom of low blood pressure.

11. The pharmaceutical composition according to claim 8, wherein the peptic ulcer is gastric ulceration or duodenal ulcer.

12. The pharmaceutical composition according to claim 8, wherein the enteritis is ulcerative colitis.

13. The pharmaceutical composition according to claim 8, wherein the kidney disorder is nephritis.

14. The method according to claim 10, wherein the peptic ulcer is gastric ulceration or duodenal ulcer.

15. The method according to claim 10, wherein the enteritis is ulcerative colitis.

16. The method according to claim 10, wherein the kidney disorder is nephritis.

* * * * *